United States Patent
Siems et al.

(10) Patent No.: US 10,653,173 B2
(45) Date of Patent: May 19, 2020

(54) METHOD FOR MASKING UNPLEASANT TASTE

(71) Applicants: Analyticon Discovery GmbH, Potsdam (DE); B.R.A.I.N. Biotechnology Research Information Network AG, Zwingenberg (DE)

(72) Inventors: Karsten Siems, Michendorf (DE); Grit Kluge, Trebbin (DE); Michael Krohn, Lorsch (DE); Katja Riedel, Bensheim (DE)

(73) Assignees: Analyticon Discovery GmbH, Potsdam (DE); B.R.A.I.N. AG, Zwingenberg (DE)

( * ) Notice: Subject to any disclaimer, the term of this patent is extended or adjusted under 35 U.S.C. 154(b) by 17 days.

(21) Appl. No.: 16/395,973

(22) Filed: Apr. 26, 2019

(65) Prior Publication Data
US 2019/0364945 A1   Dec. 5, 2019

Related U.S. Application Data

(62) Division of application No. 15/567,524, filed as application No. PCT/EP2016/058472 on Apr. 16, 2016.

(30) Foreign Application Priority Data

Apr. 22, 2015  (WO) ................ PCT/EP2015/058741
May 3, 2015    (EP) .................................... 15166154

(51) Int. Cl.
| | |
|---|---|
| A61K 47/12 | (2006.01) |
| A23L 27/00 | (2016.01) |
| A23L 27/20 | (2016.01) |
| A23L 27/30 | (2016.01) |
| A23L 27/40 | (2016.01) |
| A23F 3/40  | (2006.01) |
| A23L 2/02  | (2006.01) |
| A23L 2/56  | (2006.01) |
| A61K 33/06 | (2006.01) |

(52) U.S. Cl.
CPC .............. *A23L 27/84* (2016.08); *A23F 3/405* (2013.01); *A23L 2/02* (2013.01); *A23L 2/56* (2013.01); *A23L 27/2028* (2016.08); *A23L 27/33* (2016.08); *A23L 27/40* (2016.08); *A23L 27/86* (2016.08); *A61K 47/12* (2013.01); *A23V 2002/00* (2013.01); *A61K 33/06* (2013.01)

(58) Field of Classification Search
None
See application file for complete search history.

(56) References Cited

U.S. PATENT DOCUMENTS

| | | |
|---|---|---|
| 5,336,513 A    | 8/1994  | Riemer |
| 6,048,568 A    | 4/2000  | Im |
| 6,180,159 B1 * | 1/2001  | Villagran ................ A23F 3/163 426/573 |
| 2003/0215543 A1 * | 11/2003 | Liu ......................... A23G 4/08 426/3 |
| 2014/0080842 A1 * | 3/2014  | Krohn ................. A61K 31/235 514/259.2 |
| 2014/0363530 A1 | 12/2014 | Moon et al. |

OTHER PUBLICATIONS

Vargas et al, "Antimicrobial and Antioxidant Compounds in the Nonvolatile Fraction of Expressed Orange Essential Oil," Journal of Food Protection, vol. 62, No. 8, Aug. 1, 1999, pp. 929-932.
Kuhn et al, "Bitter Taste Receptors for Saccharin and Acesulfame K," J. Neurosci., Nov. 10, 2004, 24(45): 10260-10265.
Riera et al, Am. J. Physiol. Regul. Integr. Comp. Physiol. 293: pp. R626-R634 (2007).
Mayer et al, "Acesulfame-K," Marcel Dekker, Inc., pp. 204-205 (1991).
PubMed Report for Dehydroabietic Acid (CAS RN 1740-19-8), dated Mar. 26, 2005.

* cited by examiner

*Primary Examiner* — Craig D Ricci
(74) *Attorney, Agent, or Firm* — Dilworth & Barrese, LLP

(57) ABSTRACT

Suggested are preparations, comprising or consisting of
(a) dehydroabietic acid, a salt of dehydroabietic acid and/or an extract containing dehydroabietic acid, and
(b1) at least one sweetener that is different from saccharose and/or
(b2) at least one flavonoid and/or
(b3) at least one inorganic salt or mineral substance used in foods and/or
(b4) at least one alkaloid present in foods and/or
(b5) at least one terpene present in foods.

4 Claims, 1 Drawing Sheet

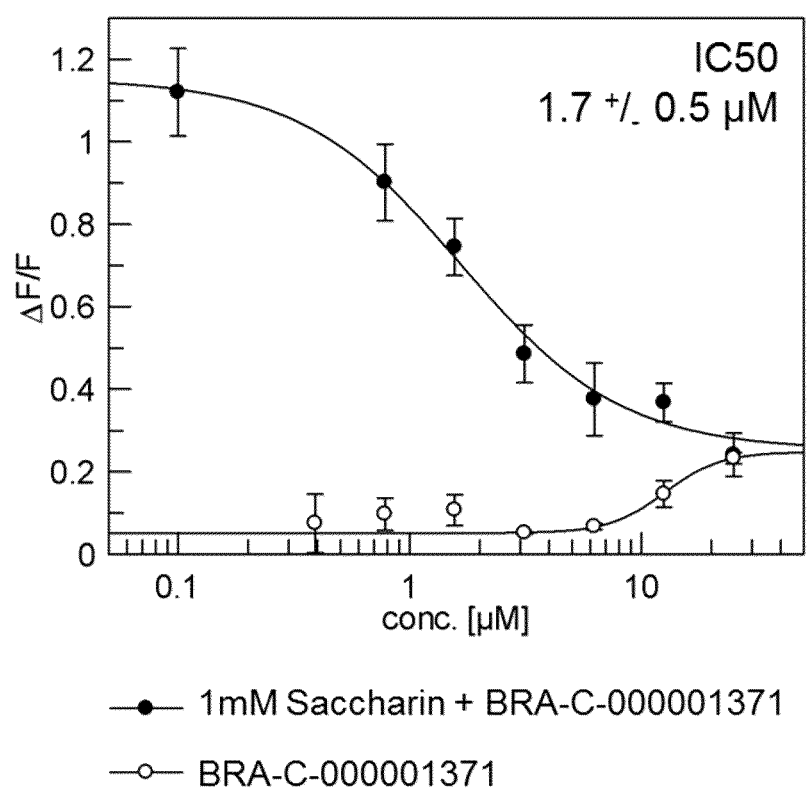

METHOD FOR MASKING UNPLEASANT TASTE

FIELD OF THE INVENTION

The invention is in the food sector and relates to new preparations containing dehydroabietic acid, substances containing these, processes for taste modulation and corresponding uses of these substances.

STATE OF THE ART

The purchasing and consuming behaviour of mostly younger consumers has been changing significantly in a time when fitness and health are increasingly gaining importance. Products are in demand which do not contain any sugar but sweeteners, which are synthetically produced such as, for example, saccharin or acesulfame-K, or which are of plant origin such as, for example, stevia, because they are calory-free and do not cause tooth decay (caries). In addition, not only the classic tea varieties such as Earl Grey have been enjoying great popularity, but also Chai teas, Mate teas and the like. Both product groups, which are so different, are sharing the same problem: synthetic or plant-based sweeteners are free from the undesired effects of sugar, but they do not convey the same taste experience. Teas, but also many fruit juice preparations, contain large amounts of flavonoids, specifically catechins and similar flavonoids, and other secondary phytonutrients such as terpenes or polyphenols, which are said to be beneficial for the human health and are therefore certainly desirable as ingredients, but which convey an intensely bitter, astringent and metallic taste, depending on their amount.

For this reason, there is an intensive demand in the market for products which are capable of masking, suppressing or modulating the unpleasant taste impressions of both sweeteners and, if used together with sweeteners, also of flavonoids, alkaloids, terpenes and other secondary phytonutrients, i.e. providing them with a pleasant taste.

Taste-modulating natural substances, including, specifically, the so-called "bitter blockers" are already known from the state of the art. For example, DE 10 2012 214560 A1 suggests 1,3-enterodiol compounds for this purpose and EP 1258200A2 suggests flavanones, particularly eriodictyol derivatives. EP 2559346 A1 discloses oleanane triterpene glycosides for the same purpose. The subject-matter of WO 2011 050955 A1 is antagonists and agonists for the human bitter taste receptors TAS2R40, hTAS2R43, hTAS2R44, hTAS2R46 and hTAS2R47, which are also terpene derivatives. WO 2013 072332 A1 reports the use of Hardwickiid acid to counteract the bitter taste.

Thus, the state of the art sufficiently describes the use of natural substances, specifically of terpene derivatives, to counteract, cover, or change undesired taste properties. However, the disadvantages of the compositions mentioned are that they require high quantities, and that they only have very specific effects, particularly with respect to synthetic sweeteners and flavonoids. In the quantities described, these substances also exhibit a taste of their own which adulterates the desired taste experience, usually with a deteriorating effect. In addition, the effectiveness of these active agents strongly depends on the matrix in which they are used. For producers of foods it is, therefore, of great importance to be able to select from a large number of alternative active agents in order to be able to determine the optimal substance for the particular purpose of application.

The object of the present invention was, therefore, to provide a natural substance which is capable of covering, neutralising, or advantageously changing unpleasant taste impressions both of sweeteners, specifically of saccharin and acesulfame-K, as well as of secondary phytonutrients such as inorganic salts, flavonoids, polyphenols, alkaloids and terpenes, specifically those which are present in various tea varieties, particularly fruit teas and herbal teas and beverages made of citrus fruit, even when present in very small quantities.

DESCRIPTION OF THE INVENTION

A first subject-matter of the invention relates to preparations, comprising or consisting of
(a) dehydroabietic acid, a salt of dehydroabietic acid and/or an extract containing dehydroabietic acid, and
(b1) at least one sweetener that is different from saccharose and/or
(b2) at least one flavonoid and/or
(b3) at least one inorganic salt or mineral used in foods and/or
(b4) at least one alkaloid present in foods and/or
(b5) at least one terpene present in foods.

Surprisingly, it was found that dehydroabietic acid fully meets the complex profile of requirements described in the beginning. It improves the taste impression in a wide range of different species of both synthetic and natural sweeteners, and also of various tea varieties and other products where unpleasant, bitter, or astringent taste impressions are caused by flavonoids, the alkaloid caffeine and the monoterpene menthol. It is a purely plant-based product which is fully effective also in very small concentrations of, for example, 25 µM (7.5 mg/l), and which thus proves to be superior to alternative prior-art substances.

Taste impressions, particularly unpleasant taste impressions which are intended to be improved within the meaning of the invention are understood as bitter and astringent taste sensations, as are other types of tastes which are, for example, described as similar to licorice. The latter are particularly found in the context of the use of stevia extracts.

BRIEF DESCRIPTION OF THE DRAWING

The present invention will be described in greater detail with reference to the accompanying FIGURE which illustrates the dose-effective relationship of dehydroabietic acid (BRA-C-000001371) in human taste cells when stimulated with saccharin.

DEHYDROABIETIC ACID

The diterpene dehydroabietic acid (component (a)) is present both in the needles and the bark, root and particularly the resin of many conifers (among others, in the plant families of Pinaceae and Juniperaceae, and here, in particular, in the genera *Pinus, Abies, Larix, Juniperus*). It is a byproduct of paper production and contained in what is referred to as tall oil.

Dehydroabietic acid has also been isolated from other plant families (e.g., from the genera *Illicium, Liquidambar, Styrax, Callicarpa, Rosmarinus, Salvia, Commiphora, Boswellia*). Dehydroabietic acid is most frequently found in resins (e.g., *Liquidambar, Styrax, Boswellia, Commiphora, Colophony*, but also in amber).

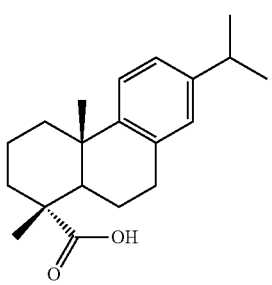 [SMILES: CC(C)c1ccc2c(c1)CCC1[C@](C)(C(=O)O)CCC[C@]21C]

Structural Formula of Dehydroabietic Acid (CAS 1740-19-8)

The content of dehydroabietic acid in pine resin is mostly below 10%, but it may also be increased to a content of >50%, using a method that is known by the skilled person as disproportionation (e.g., according to the process described by Song et al in JOURNAL OF WOOD CHEMISTRY AND TECHNOLOGY, 5(4), 535-542 (1985)).

Both enantiomers of dehydroabietic acid are known (CAS 1740-19-8 and CAS 6980-63-8). The term "dehydroabietic acid" is understood as meaning the isomers and any optional enantiomeric mixtures within the meaning of the present invention.

Although extracts containing dehydroabietic acid as well as the commercially available technical dehydroabietic acid having a purity of about 85% can be used, the use of high-purity products is preferred, which have a content of dehydroabietic acid of at least 90% by weight, preferably at least 95% by weight, and particularly preferably from about 95 to about 99% by weight. These high-purity products are obtainable by the typical work-up procedures of preparative organic chemistry so that the skilled person is not required to make an inventive step. In the following, a corresponding process is described, by way of example, in example 1.

Instead of using dehydroabietic acid itself, it is also possible to use its salts, specifically its alkali and ammonium salts, particularly the sodium salt.

The invention also comprises the use of extracts containing dehydroabietic acid, the production of which also forms part of the skilled person's tools, and which is described, by way of example, in example 2 below. Preferably, these extracts contain at least 20% by weight, more preferably at least 30% by weight, and particularly preferably from about 40 to about 60% by weight dehydroabietic acid.

Sweeteners

Suitable sweeteners or sweet-tasting additives forming group (b) are, firstly, carbohydrates such as, for example, trehalose, lactose, maltose, melizitose, raffinose, palatinose, lactulose, D-fructose, D-glucose, D-galactose, L-rhamnose, D-sorbose, D-mannose, D-tagatose, D-arabinose, L-arabinose, D-ribose, D-glyceraldehyde or maltodextrin. Plant-based preparations containing these substances are also suitable, for example, on the basis of sugarbeet (*Beta vulgaris* ssp., sugar fractions, sugar syrup, molasses), sugar cane (*Saccharum officinarum* ssp., molasses, sugar cane syrup), maple syrup (*Acer* ssp.) or agave (agave syrup).

Suitable are also synthetic, i.e. usually enzymatically produced starch or sugar hydrolysates (invert sugar, fructose syrup) as well as natural or synthetic sweet-tasting substances, such as Fruit concentrates (e.g., on the basis of apples or pears);
Sugar alcohols (e.g., erythritol, threitol, arabitol, ribotol, xylitol, sorbitol, mannitol, dulcitol, lactitol);
Proteins (e.g., miraculin, monellin, thaumatin, curculin, brazzein);
Sweeteners (e.g., magap, sodium cyclamate, acesulfame-K, neohesperidin dihydrochalcone, saccharine sodium salt, aspartame, superaspartame, neotame, alitame, sucralose, stevioside, rebaudioside, lugduname, carrelame, sucrononate, sucrooctate, monatin, phenylodulcin);
Sweet-tasting amino acids (e.g., glycine, D-leucine, D-threonine, D-asparagine, D-phenylalanine, D-tryptophan, L-proline);
Further sweet-tasting low-molecular substances such, e.g., hernandulcin, phyllodulcin, dihydrochalcon glycoside, glycyrrhizin, glycerrhetinic acid and its derivatives and salts, rubusosides, mogrosides
Extracts of sweet-tasting plants such as *Stevia rebaudiana*, *Glycyrrhiza* ssp. (liquorice), *Lippia dulcis*, *Momordica grosvenori*.

The sweeteners may also be plant extracts, as is described by way of example in the following.

Rebaudiosides are among the steviosides, which are the main components of the plant *Stevia rebaudiana*, which is also referred to as sweet weed or honey weed.

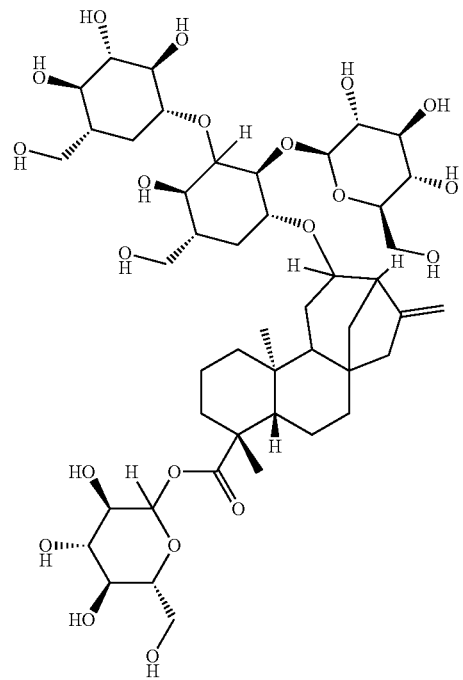

Rebaudiosides

10% of the dry matter of the leaves are constituted by the diterpene glycoside stevioside, followed by rebaudioside A (2 to 4% by weight) as well as by more than ten other steviol glycosides such as dulcoside. By now, most countries have approved rebaudiosides and *stevia* extracts for use as sweeteners; a daily uptake of up to 4 mg stevioside per kilogramme of bodyweight is considered harmless. Within the meaning of the invention, individual rebaudiosides or the extracts of the *stevia* plant may be used. Particularly preferred, however, is the use of rebaudioside A, as this substance has a lower bitterness and the highest sweetening power. The substance mixtures according to the invention may contain components (a) and (b) in a weight ratio from about 1:99 to about 99:1, preferably from about 25:75 to about 75:25, and particularly preferably from about 40:60 to about 60:40.

Also the dihydrochalcones represent flavonoids, in which particularly the two representatives naringenin dihydrochalcone and neohesperidin dihydrochalcone must be highlighted, which are known as synthetic sweeteners:

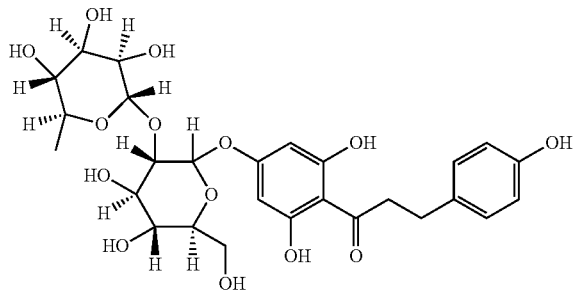

Neohesperidin dihydrochalcone

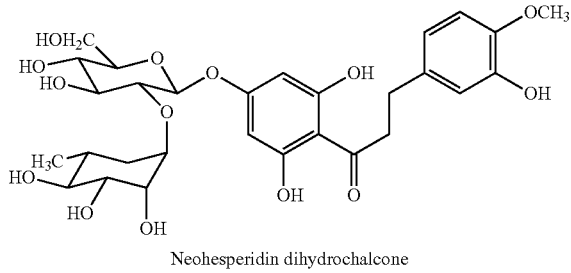

Neohesperidin dihydrochalcone

A group of cucurbitane glycosides is referred to as mogrosides, which are known as a component of the natural sweetener Luo Han Guo. Mogroside-V, which is 400 times sweeter than sugar, is highlighted herein.

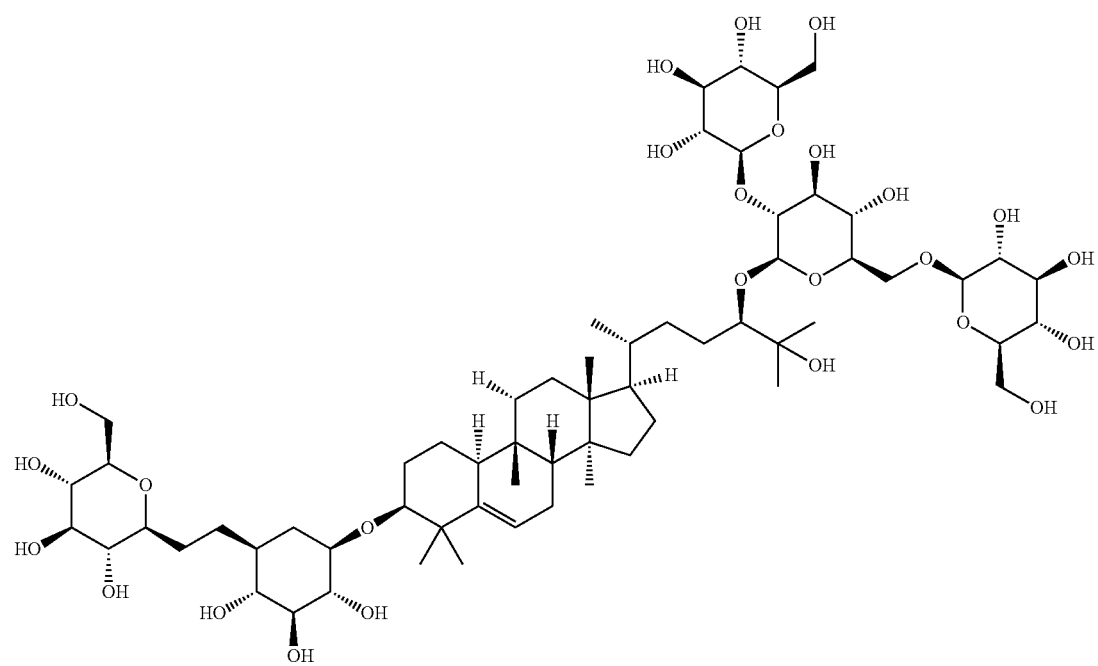

Mogroside-V

Eventually, suitable sweeteners also include extracts of the plants which are selected from the group consisting of *Rubus allegheniensis, Rubus arcticu, Rubus strigosus, Rubus armeniacus, Rubus caesius, Rubus chamaemorus, Rubus corylifolius* agg., *Rubus fruticosus* agg., *Rubus geoides, Rubus glaucus, Rubus gunnianus, Rubus idaeus, Rubus illecebrosus, Rubus laciniatus, Rubus leucodermis, Rubus loganobaccus, Rubus loxensis, Rubus nepalensis, Rubus nessensis, Rubus nivalis, Rubus odoratus, Rubus pentalobus, Rubus phoenicolasius, Rubus saxatilis, Rubus setchuenensis, Rubus spectabilis* and *Rubus ulmifolius* and their mixtures. These are substantially extracts of various

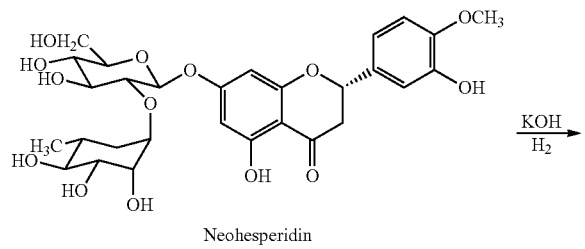

Neohesperidin blackberry and raspberry varieties having a content in rubosides. Extracts of *Rubus suavissimus* are preferred.

A further active agent in this group is glycyrrhetinic acid, or a corresponding salt, or an extract containing this substance.

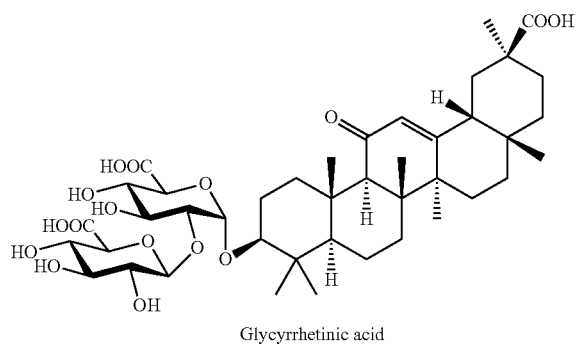

Glycyrrhetinic acid

Within the meaning of the invention, it is possible to use the acid itself, its salts—for example, sodium, potassium, or ammonium salt—or the extracts of the plant *Glycyrrhiza glabra*. Mono ammonium glycyrrhizinate is particularly preferred.

Preferred sweeteners, the taste perception of which is to be improved, are selected from the group consisting of saccharin, acesulfame-K, steviol glycosides, particularly rebaudioside A, and stevia extracts.

Flavonoids

The flavonoids forming component (1b) are mostly catechins, which are mainly contained in tea in varying quantities and compositions, and which are among the most powerful bitter principles. Herein, the most important representatives are:

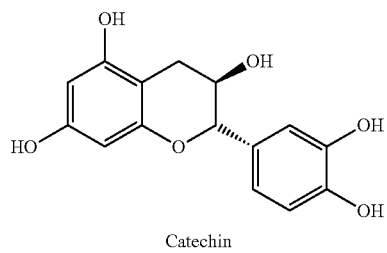

Catechin

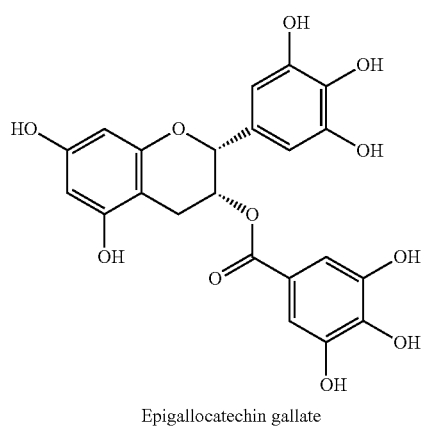 [SMILES: O=C(O[C@@H]1Cc2c(O)cc(O)cc2O[C@@H]1c1cc(O)c(O)c(O)c1)c1cc(O)c(O)c(O)c1]

Epigallocatechin gallate as well as epicatechin and gallocatechin. In addition to the flavonoids and their oligomers and oxidation products, also the alkaloid caffeine contributes to the bitter taste of green and black tea. In beverages made of citrus fruit, the bitter or astringent taste is mainly caused by polymethoxylated flavones such as sinensetin and nobiletin, glycosylated flavonoids, e.g., naringin, and by terpenes of the limonoid type, e.g., limonene.

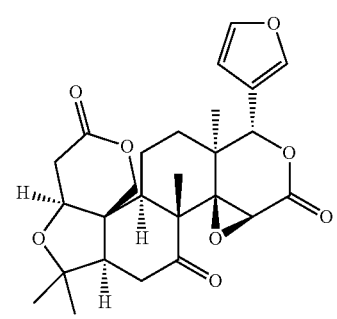

Limonene

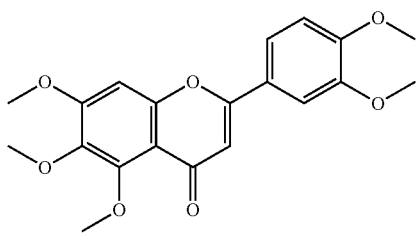

Sinensetin

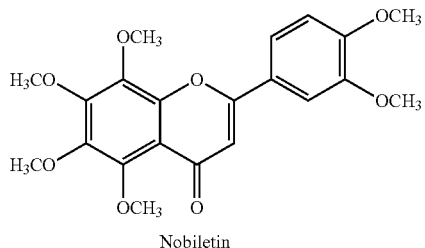

Nobiletin

Mineral Substances

Magnesium is an important mineral substance. Undersupply with magnesium is often not diagnosed, but it may appear as a side effect in many diseases (e.g., diabetes, hypertension). Senior citizens and pregnant women frequently have an increased demand for magnesium. An increased demand for magnesium may be balanced by mineral supplements or by adding magnesium to foods, e.g., bread that is specifically produced for senior citizens.

Magnesium may be taken in the form of various salts, e.g., as magnesium chloride or magnesium sulfate. Magnesium-containing salts taste bitter, particularly magnesium sulfate, which is also referred to as epsomite.

Potassium is also added to foods, but usually not with the intention to balance a potassium deficiency, but as a substitute for salt in order to reduce the sodium content in foods while maintaining the taste of salt. As potassium chloride has a bitter taste, only part of the sodium may be substituted by potassium. In order to reduce the bitter taste of potassium chloride, for example, ascorbic acid, fumaric acid and citric acid, or various sugars (lactose, dextrose), or yeast extract may be added (cf. DE3035518C2). However, these solutions are only suitable for some foods, as they are not neutral with regard to their taste or may lead to an increased uptake of calories, which is not desired in sodium-chloride reduced foods which are, therefore, healthier.

Preparations

Preparations of the present invention may contain components (a), based on component (b), in concentrations of about 1 to about 500 μM, preferably, about 10 to about 250 μM, particularly preferably, about 20 to about 100 μM.

A form of preparation which is intended for commercial distribution and which is particularly suitable, for example, in form of a sweetener tablet typically contains 1 to 40 mg sweetener(s), e.g., saccharin or acesulfame-K, and 1 to 30 mg dehydroabietic acid, based on a total weight of the tablet of 60 mg where the difference in quantity is represented by tableting additives, particularly binders. One of these tablets corresponds to the sweetening power of one sugar cube and is completely sufficient to sweeten, for example, a common cup of tea, completely masking the unpleasant taste that is linked with the addition of a sweetener in the process.

Foods

A further subject-matter of the present invention relates to foods which contain the preparations according to the invention. In this case it is possible to add the components individually or together, where the addition of the mixture is preferred. With respect to the taste improvement in flavonoids, component (a) can be used alone or as a mixture of (a) and (b).

Examples for foods, in principle, comprise baked goods, e.g. bread, dry biscuits, cakes, other baked products, confectionery (e.g. chocolates, chocolate bar products, other bar products, fruit gum, hard and soft caramels, chewing gum), alcoholic or nonalcoholic beverages (for example, coffee, tea, iced tea, wine, wine-containing beverages, beer, beer-containing beverages, liqueurs, schnapps, brandies, fruit-containing (carbonated) beverages, isotonic (carbonated) beverages, refreshing (carbonated) beverages, nectars, spritzers, fruit and vegetable juices, fruit or vegetable juice formulations), instant beverages (for example, instant cocoa beverages, instant tea beverages, instant coffee beverages, instant fruit beverages), meat products (for example, ham, fresh sausage or uncooked sausage formulations, seasoned or marinated fresh or salted meat products), eggs or egg products (dried egg, egg white, egg yolk), cereal products (for example, breakfast cereals, muesli bars, precooked ready-made rice products), dairy products (for example, milk beverages, butter milk beverages, milk ice cream, yoghurt, kefir, fresh cheese, soft cheese, hard cheese, dried milk powder, whey, whey beverages, butter, buttermilk, products containing partly or completely hydrolysed milk protein), products from soy protein or other soy bean fractions (for example, soy milk and products produced therefrom, fruit beverages with soy protein, soy lecithin-containing formulations, fermented products such as tofu or tempeh or products produced therefrom, soy sauces), products made of other plant-based protein sources, for example, oat protein beverages, fruit formulations (for example, preserves, fruit ice cream, fruit sauces, fruit fillings), vegetable formulations (for example, ketchup, sauces, dried vegetables, frozen vegetables, precooked vegetables, vegetables preserved in vinegar), snack products (for example, baked or fried potato crisps/chips or products based on potato dough, extrudates on a maize or peanut basis), products on a fat and oil basis, or emulsions of the same (for example, mayonnaise, remoulade, dressings), other ready meals and soups (for example, dried soups, instant soups, pre-cooked soups), condiments, seasoning mixtures and, particularly, seasonings, which are used, for example, in the snack industry.

Preferably, however, it is soft drinks or hot drinks or instant drinks such as, for example, teas or fruit juices.

Pharmaceutical Preparations

The taste problem described above does not only appear in foods with added non-sugar sweeteners, but also in pharmaceutical products in which the frequently repulsive taste of the active agent needs to be masked particularly carefully. Therefore, a further subject-matter of the invention also relates to pharmaceutical preparations, containing the preparations according to the invention. Also in this case, it is preferred to add component (a) and (b) as a mixture. Preferably, the pharmaceutical preparations are liquid products, particularly cough syrup, antipyretic agents, or antibiotics. Liquid forms of medication are particularly used in children and where the masking of the bitter taste of the active agent is technologically impossible, for example, when applying capsules, tablets or other solid forms of pharmaceuticals.

Both the foods and the pharmaceutical preparations may contain dehydroabietic acid or a salt of dehydroabietic acid in concentrations from about 1 to about 500 μM, preferably, about 10 to about 250 μM, particularly preferably about 20 to about 100 μM.

INDUSTRIAL APPLICATION

A further subject-matter of the invention relates to a process for masking unpleasant taste impressions of sweeteners and/or flavonoids and/or terpenes and/or alkaloids and/or mineral salts as well as foods or pharmaceutical preparations containing these substances, characterised in that a quantity of a dehydroabietic acid, a salt of dehydroabietic acid and/or an extract containing dehydroabietic acid is added to them.

Preferably, dehydroabietic acid, a salt of dehydroabietic acid and/or an extract containing dehydroabietic acid is added in quantities such that the concentration of dehydroabietic acid in the product is from about 1 to about 500 μM, preferably about 10 to about 250 μM, more preferably about 20 to about 150 μM and particularly preferably about 50 to about 100 μM.

The use of dehydroabietic acid, a salt of dehydroabietic acid and/or an extract of dehydroabietic acid is also claimed for masking unpleasant taste impressions of sweeteners and/or flavonoids and/or terpenes and/or alkaloids and/or mineral salts as well as foods or pharmaceutical preparations containing these substances, in the process of which dehydroabietic acid, a salt of dehydroabietic acid and/or an extract containing dehydroabietic acid is added to these such that the concentration of dehydroabietic acid in the product is from about 1 to about 500 μM, preferably about 10 to about 250 μM, particularly preferably about 20 to about 100 μM.

EXAMPLES

Example 1

Purification of Dehydroabietic Acid 2 g of commercially available dehydroabietic acid (CAS 1740-19-8, purchased from Interchim, 211 bis AVENUE KENNEDY, BP 1140, 03103 MONTLUCON CEDEX, France) with a content of ca. 85% was purified by preparative HPLC chromatography as follows.

| | |
|---|---|
| Separation number: | H-2074-B |
| Stationary phase: | LichrospherSelect B, 10 μm, 250 × 50 mm |

-continued

| Mobile phase A: | 5 mMol ammonium formate buffer, set to pH 3.0 with formic acid |
|---|---|
| Mobile phase B: | methanol - acetonitril 1:1 (v/v) with 5 mMol ammonium formate |
| Gradient: | from 62% to 81% B in 57 min |
| Flow rate: | 80 ml/min |
| Detection: | ELSD |

Fractions containing the product were combined, the solvent was evaporated in a vacuum, and the isolated dehydroabietic acid was analytically characterised by means of H-NMR spectroscopy and LC-MS. The identity of the isolated dehydroabietic acid was confirmed by the NMR and the molecular mass, the purity was at >98%.

The LC-MS method for analytical characterisation of the isolated substance is summarised in the following Table 1:

TABLE 1

LC-MS method

| HPLC system | PE Series 200 |
|---|---|
| MS system | Applied Biosystems API 150 |
| Data system | Analyst 1.3 |
| Stationary phase | Merck Select B 250 × 4 mm, 5 µm |
| Flow rate | 1 ml/min |
| Detection | (+/(−) - ESI, Fast-Switching-Mode ELSD (Sedex 75) UV (Merck, 254 nm) |
| Sample concentration | 10 mg/ml in DMSO |
| Injection volume | 30 µl |
| Mobile phase: | A: 5 mM ammonium formate and 0.1% formic acid B: acetonitrile/methanol = 1:1, 5 mM ammonium formate and 0.1% formic acid (pH 3) |
| Gradient | Time [min]   % A   % B 00.0          85    15 30.0           0   100 35.0           0   100 |

Example 2

Production of an Extract Containing Dehydroabietic Acid 10 g commercially available colophony resin (purchased from Alfred Galke GmbH, Am Bahnhof 1, 37539 Bad Grund, order number 36004) is extracted with a mixture of MTB ether and methanol (1:1 v/v), removing the solvent in a vacuum. The extract contains ca. 25% dehydroabietic acid.

Example 3

In-Vitro Assay

Human bitter receptor cells were established, and the activation of these cells was quantified in order to detect, by means of a cell-based test system, natural substances which reduce the bitterness of bitter principles. The change of the intracellular potassium level was measured for quantitation of the activation of bitter receptor cells.

Establishment of the Cell-Based Measurement System

In order to detect substances with inhibitory activity, a high-throughput cell-based in-vitro measurement system was established. To this end, a human bitter receptor cell line was used that was produced for this application based on Hochheimer, A., Krohn, M., Rudert, K., Riedel, K., Becker, S., Thirion, C. and Zinke, H. "Endogenous gustatory responses and gene expression profile of stably proliferating human taste cells isolated from fungiform papillae" Chem Senses, 39, 359-377 (2014).

Quantitation of the Intracellular Calcium Level in the Cell-Based Measurement System A human bitter receptor cell line having endogeneous bitter receptors was used for a screening for antagonists in a high-throughput format. The modulation of the intracellular potassium level of the bitter receptor cells was quantitated by means of the potassium-sensitive fluorescence dye Fluo-4 AM in a microplate reader. The activation of the bitter receptor cells by an agonist leads to an increase of the intracellular potassium level. The quantity of mobilised calcium may be quantitated by means of fluorescence, which increases in proportion with the concentration of calcium. In case of inhibition by an antagonist, the quantity of mobilised calcium is significantly lower, as is the change of fluorescence induced by an agonist.

Performance of the Process:

Human bitter receptor cells were cultivated in a cell cultivation medium in a steam-saturated atmosphere at 37° C. and with 5% $CO_2$. The cells were seeded at a density of 20,000 cells per well in a 96-well plate. 24 hours after seeding, the cells were dyed with 4 µM of the calcium-sensitive fluorescence dye Fluo-4 AM in HBSS (Hank's Balanced Salt Solution) buffer, and the mobilisation of calcium in living cells was measured in the microplate reader (FlexStation® Systenn, Molecular Devices).

Screening for Antagonists:

Parallel to this, human bitter receptor cells were stimulated with 1-5 mM of the bitter principle saccharin (agonist) and with 10 µM of the potential antagonists. The mobilisation of calcium was measured in the microplate reader at 37° C.

Analysis:

The mobilisation of calcium was quantitated as the change of fluorescence (dF) after the addition of the substance, taking into account the basal fluorescence (F0) as dF/F0. The relative fluorescence units (dF/F0), measured after stimulation with agonist and antagonist, were compared with the sole stimulation by the agonist (positive control). In doing so, active substances that are lowering the calcium level were identified. Potential antagonists were repeatedly tested for their activity. Data processing and analysis was performed with a software program of the microplate reader (SoftMax® Pro Software, Molecular Devices).

Determination of the Dose-Effect Relationship of Antagonists

In order to determine the average inhibitory concentration (IC50) of the antagonist, human bitter taste receptors were stimulated with 0.1-25 µM of the substance in the presence of the agonist. A representative dose-effect relationship is illustrated in FIG. 1. It indicates the dose-effect relationship of dehydroabietic acid (BRA-C-00001371) in human taste cells when stimulated with 1 mM saccharin (fluorometric detection) IC50 1.7+/−0.5 µM.

Example 4

The Natural Taste of High-Purity Dehydroabietic Acid and of Extracts Containing Dehydroabietic Acid The sensory evaluation of the samples was performed by a panel of five experienced assessors. The sensory tests were performed descriptively, randomized, blinded, and by means of a "sip and spit" method. To this end, the sample is moved within the mouth for a few seconds to evaluate its taste, and it is not swallowed but expectorated. The results may be taken from the following Table 2a:

TABLE 2a

Tasting of high-purity dehydroabietic acid

| | |
|---|---|
| Test method | Descriptive evaluation, "sip and spit" method, blinded and randomised samples, pH neutral |
| Test sample | Purified dehydroabietic acid, purity >98% |
| Panelists | 3-5 experienced assessors |
| Preparation of the samples | Three different concentrations (10 μM, 50 μM, and 100 μM) dissolved in 0.5% ethanol, comparative sample 0.5% ethanol in water |
| Evaluation | 10 μM neutral |
| | 50 μM astringent, dry, slightly metallic taste |
| | 100 μM Slightly cooling feeling on the tongue, astringent, dry, slightly bitter, not sweet, slightly masking the taste of ethanol |

TABLE 2b

Tasting of extracts containing dehydroabietic acid

| | | | | |
|---|---|---|---|---|
| Test method | Descriptive evaluation, "sip and spit" method, blinded and randomised samples, pH neutral | | | |
| Test sample | 1) purified dehydroabietic acid, purity >98% 2) commercially available dehydroabietic acid, purity 85% (HPLC) 3) extract with ca. 25% dehydroabietic acid | | | |
| Panelists | 3-5 experienced assessors | | | |
| Preparation of the samples | Three different concentrations (dissolved in 0.5% ethanol), comparison sample 0.5% ethanol in water, final concentration of the ethanol below 0.5% | | | |
| Evaluation | Conc. | Sample 1 | Sample 2 | Sample 3 |
| | 3 mg/l | neutral | neutral | neutral |
| | 7.5 mg/l | neutral | neutral | slightly bitter |
| | 30 mg/l | slightly bitter | slightly bitter | More bitter than samples 1 and 2, resinous |

Example 5

Taste of the Combination of Dehydroabietic Acid with Saccharin

The sensory evaluation of the samples was performed by a team of five experienced assessors. The results may be taken from the following Table 3:

TABLE 3

Tasting of high-purity dehydroabietic acid + saccharin

| | |
|---|---|
| Test method | Descriptive and discriminative evaluation, "sip and spit" method, blinded and randomised samples, pH neutral |
| Test sample | Purified dehydroabietic acid, purity >98% |
| Panelists | 3-5 experienced assessors, trained to recognise the taste of saccharin and acesulfame-K |
| Preparation of the samples | Three different concentrations of dehydroabietic acid (10 μM, 25 μM, and 50 μM) with 80 ppm saccharin (corresponding to a 3% saccharose-equivalent) dissolved in 0.5% ethanol, 80 ppm saccharin, comparison sample 0.5% ethanol in water, final concentration of the ethanol below 0.5% |
| Evaluation | 10 μM Slightly bitter aftertaste |
| | 25 μM Less bitter with a very clear taste profile, less dry |
| | 50 μM Less bitter, significantly less aftertaste than in 10 p.M |

Example 6

Taste of the Combination of Dehydroabietic Acid with Acesulfame-K

The sensory evaluation of the samples was performed by a team of five experienced assessors. The results may be taken from the following Table 4:

TABLE 4

Tasting of high-purity dehydroabietic acid + acesulfame-K

| | |
|---|---|
| Test method | Descriptive and discriminative evaluation, "sip and spit" method, blinded and randomised samples, pH neutral |
| Test sample | Purified dehydroabietic acid, purity >98% |
| Panelists | 3-5 experienced assessors, trained to recognise the taste of saccharin and acesulfame-K |
| Preparation of the samples | Three different concentrations of dehydroabietic acid (10 μM, 25 μM, and 50 μM) with 150 ppm acesulfame-K (corresponding to a 3% saccharose equivalent) dissolved in 0.5% ethanol, 150 ppm acesulfame-K comparison sample 0.5% ethanol in water, final concentration of the ethanol below 0.5% |
| Evaluation | 10 μM Very full taste impression, significantly less bitter, masking the astringent and metallic taste |
| | 25 μM No bitter taste present any more |
| | 50 μM Clear taste impression, delays the increasing formation of a bitter and acid taste. |

Example 7

Taste Modulation of Black Tea

The sensory evaluation of the samples was performed by a team of five experienced assessors. Details may be taken from the following Table 5:

TABLE 5

Tasting of Black tea

| | |
|---|---|
| Test method | Descriptive and discriminative evaluation, "sip and spit" method, blinded and randomised samples, pH neutral |
| Test sample | Purified dehydroabietic acid, purity >98% |
| Panelists | 5 experienced assessors |
| Preparation of the samples | Two different concentrations of dehydroabietic acid (25 μM and 50 μM) dissolved in ethanol, 1 tea bag of Earl Grey, allowed to steep in 100 ml water for 10 min, addition of the stock solution at ca. 20° C., end concentration of ethanol below 0.5%, comparison sample 0.5% ethanol in tea |
| Evaluation | 25 μM Slightly less bitter than the comparison example |
| | 50 μM Significantly less bitter, a little less astringent than the comparison example |

Example 8

Taste Modulation of Green Tea

The sensory evaluation of the samples was performed by a team of five experienced assessors. Details may be taken from the following Table 6:

TABLE 6

Tasting of Green tea

| | |
|---|---|
| Test method | Descriptive and discriminative evaluation, "sip and spit" method, blinded and randomised samples, pH neutral |

TABLE 6-continued

| | Tasting of Green tea |
|---|---|
| Test sample | Purified dehydroabietic acid, purity >98% |
| Panelists | 5 experienced assessors |
| Preparation of the samples | Two different concentrations of dehydroabietic acid (25 µM and 50 µM) dissolved in ethanol, 3 g of Green tea, allowed to steep in 250 ml water for 5 min, addition of the stock solution at ca. 20° C., end concentration of ethanol below 0.5%, comparison sample 0.5% ethanol in tea |
| Evaluation | 25 µM Slightly bitter taste that quickly fades |
| | 50 µM As in 25 µM, but less astringent |

Example 9

Taste Modulation of Grapefruit Juice

The sensory evaluation of the samples was performed by a team of five experienced assessors. Details may be taken from the following Table 7:

TABLE 7

| | Tasting of grapefruit juice |
|---|---|
| Test method | Descriptive and discriminative evaluation, "sip and spit" method, blinded and randomised samples, pH neutral |
| Test sample | Purified dehydroabietic acid, purity >98% |
| Panelists | 5 experienced assessors |
| Preparation of the samples | Two different concentrations of dehydroabietic acid (25 µM and 50 µM) dissolved in ethanol, grapefruit juice (grocery store, from concentrate), addition of the stock solution at ca. 20° C., end concentration of the added ethanol below 0.5%, pH of the test sample 3.6, comparison sample 0.5% ethanol in grapefruit juice |
| Evaluation | 25 µM Significantly less bitter than the comparison sample, clearly more aromatic |
| | 50 µM Significantly less bitter than the comparison sample, no negative influence of the fruit taste |

Experiments involving freshly squeezed grapefruit juice also exhibited a significant reduction of the bitter taste without negatively influencing the fruit aroma and the refreshing tartness.

Example 10

Taste Modulation of a Mineral Salt Solution

The sensory evaluation of the samples was performed by a team of five experienced assessors. Details may be taken from the following Table 8:

TABLE 8

| | Tasting of a mineral salt solution |
|---|---|
| Test method | Descriptive and discriminative evaluation, "sip and spit" method, blinded and randomised samples, pH neutral |
| Test sample | Purified dehydroabietic acid, purity >98% |
| Panelists | 5 experienced assessors |
| Preparation of the samples | Two different concentrations of dehydroabietic acid (25 µM and 50 µM) dissolved in ethanol, 2 g MgCl$_2$ (Lohmann) dissolved in 100 ml water, addition of the stock solution at ca. 20° C., end concentration of the ethanol below 0.5%, comparison sample: mineral salt solution containing 0.5% ethanol |

TABLE 8-continued

| | Tasting of a mineral salt solution |
|---|---|
| Evaluation | 25 µM Almost no difference to the comparison sample |
| | 50 µM Significantly less bitter than the comparison sample |

Example 11

Taste Modulation of a Solution Containing Potassium Chloride

The sensory evaluation of the samples was performed by a team of five experienced assessors. Details may be taken from the following Table 9:

TABLE 9

| | Tasting of a potassium chloride solution |
|---|---|
| Test method | Descriptive and discriminative evaluation, "sip and spit" method, blinded and randomised samples, pH neutral and 3.2, comparison example: 0.5% ethanol in potassium chloride solution at a corresponding pH value |
| Test sample | Purified dehydroabietic acid, purity >98% |
| Panelists | 5 experienced assessors |
| Preparation of the samples | Two different concentrations of dehydroabietic acid (25 µM and 50 µM) dissolved in ethanol, 1,500 mg KCl dissolved in 100 ml water, pH value was adjusted by citric acid, addition of the stock solution at ca. 20° C., end concentration of ethanol below 0.5% |
| Evaluation | 25 µM pH neutral Almost no difference to the comparison sample (bitterness and saltiness) |
| | 25 µM pH 3.2 Almost no difference to the comparison sample (bitterness) Saltier than the comparison sample More pronounced tartness than the comparison sample |
| | 50 µM pH neutral Less bitter than the comparison sample |

Example 12

Taste Modulation of a Stevia/Rebaudioside a Solution

The sensory evaluation of the samples was performed by a team of five experienced assessors. Details may be taken from the following Table 10:

TABLE 10

| | Tasting of stevia/rebA solution |
|---|---|
| Test method | Descriptive and discriminative evaluation, "sip and spit" method, blinded and randomised samples, pH 3.2 and pH neutral |
| Test sample | purified dehydroabietic acid, purity >98% |
| Panelists | 5 experienced assessors |
| Preparation of the samples | Dehydroabietic acid (25 µM) dissolved in ethanol, 24 mg (stevia-rebA commercially available, equivalent to 6% saccharose) dissolved in 100 ml water, pH value was adjusted by means of citric acid, addition of the stock solution at ca. 20° C., end concentration of the ethanol below 0.5%, comparison example 0.5% ethanol in stevia/rebA solution |
| Evaluation | 25 µM pH neutral Slightly less bitter than the comparison sample Sweeter and fuller taste profile than the comparison sample |

TABLE 10-continued

Tasting of stevia/rebA solution

| | |
|---|---|
| 25 µM<br>pH 3.2 | Unpleasant taste (bitterness and licorice aroma) reduced, sweeter and fuller taste profile than comparison sample |

Example 13

Taste Modulation of a Naringin Solution

The sensory evaluation of the samples was performed by a team of five experienced assessors. Details may be taken from the following Table 11:

TABLE 11

Tasting of the naringin solution

| | | |
|---|---|---|
| Test method | Descriptive and discriminative evaluation, "sip and spit" method, blinded and randomised samples, pH 3.2 and pH neutral | |
| Test sample | Purified dehydroabietic acid, purity >98% | |
| Panelists | 5 experienced assessors | |
| Preparation of the samples | Dehydroabietic acid (25 µM) dissolved in ethanol, 300 mg naringin dissolved in 100 ml water, pH value was adjusted by means of citric acid, addition of the stock solution at ca. 20° C., end concentration of ethanol below 0.5%, comparison sample 0.5% ethanol in the naringin solution | |
| Evaluation | 25 µM<br>pH neutral | More aromatic taste profile than the comparison example Unpleasant aftertaste (astringency) clearly reduced |
| | 25 µM<br>pH 3.2 | Unpleasant aftertaste reduced, less bitter than comparison example, same astringency as comparison example. |

Example 14

Taste Modulation of Menthol in a Lozenge

The sensory evaluation of the samples was performed by a team of five experienced assessors. Details may be taken from the following Table 12:

TABLE 12

Tasting of menthol lozenges

| | | |
|---|---|---|
| Test method | Descriptive and discriminative evaluation, "sip and spit" method, blinded and randomised samples, pH 3.2 and pH neutral | |
| Test sample | Purified dehydroabietic acid, purity >98% | |
| Panelists | 5 experienced assessors | |
| Preparation of the samples | Dehydroabietic acid (25 µM) dissolved in ethanol, 0.3% menthol were formulated in a lozenge, pH value was adjusted by means of citric acid, addition of the stock solution at >100° C., end concentration of the ethanol below 0.5%, comparison samples were lozenges without dehydroabietic acid | |
| Evaluation | 25 µM<br>pH neutral | Sweeter and significantly lower astringency than the comparative example Fuller taste profile and better aroma than the comparative example |
| | 25 µM<br>pH 3.2 | Astringency comparable, unpleasant aftertaste reduced, less bitter than the comparative example |

The invention claimed is:

1. A method for masking unpleasant, bitter, astringent and/or liquorice-like taste impressions of one or more artificial sweeteners in a food or pharmaceutical preparation, said method comprising adding dehydroabietic acid in an amount of about 1 µM to about 500 µM to said food or pharmaceutical preparation, wherein said food or said pharmaceutical preparation does not comprise caffeine, and wherein said dehydroabietic acid masks the unpleasant, bitter, astringent and/or liquorice-like taste impressions of said one or more artificial sweeteners contained therein, with the proviso that the food preparation is not a chewing gum.

2. The method of claim 1 wherein the artificial sweetener is selected from the group consisting of acesulfame K, aspartame, superaspartame, neotame, alitame, saccharine, sucralose, cyclamate, sucrononate, carrelame, lugduname, and combinations thereof.

3. The method of claim 1 wherein the food preparation is selected from the group consisting of a soft drink, a hot drink, and an instant drink.

4. The method of claim 1 wherein the pharmaceutical preparation is a liquid preparation.

* * * * *